(12) United States Patent
Krjutskov et al.

(10) Patent No.: US 7,638,310 B2
(45) Date of Patent: Dec. 29, 2009

(54) METHOD TO DETERMINE SINGLE NUCLEOTIDE POLYMORPHISMS AND MUTATIONS IN NUCLEIC ACID SEQUENCE

(75) Inventors: Kaarel Krjutskov, Tartu (EE); Andres Metspalu, Tartu (EE)

(73) Assignee: Estonian Biocenter, Tartu (EE)

( * ) Notice: Subject to any disclaimer, the term of this patent is extended or adjusted under 35 U.S.C. 154(b) by 215 days.

(21) Appl. No.: 12/011,235

(22) Filed: Jan. 25, 2008

(65) Prior Publication Data
US 2009/0048119 A1    Feb. 19, 2009

Related U.S. Application Data (63) Continuation-in-part of application No. PCT/EE2007/000003, filed on Mar. 6, 2007.

(51) Int. Cl.
C12Q 1/68    (2006.01)
C12P 19/34    (2006.01)

(52) U.S. Cl. .......................... 435/91.2; 435/6; 435/91.1

(58) Field of Classification Search ........................ None
See application file for complete search history.

(56) References Cited

U.S. PATENT DOCUMENTS 6,287,778 B1 * 9/2001 Huang et al. .................... 506/4
6,448,020 B1    9/2002 Toftgard et al.

OTHER PUBLICATIONS

Shumaker, J.M. et al. 2001. APEX disease gene resequensing: Mutation in exon 7 of the p53 tumor suppressor gene. Bio Organic and Medical Chemistry 9 (9) 2269-2278.
Kurg A. et al. 2000. Arrayed primer extension: solid-phase four color DNA resequencing. adn mutation detection tech. Genetic testing, Larchmont NY US vol. 4, No. 1 pp. 1-7.
Tebbut, Scot J. et al. 2005. SNP Chart: an integrated platform for visualizatonand interpretation of microarray genotyping data. Bioinformatics 21(1): 124-127.
Podder Mohua et al. 2006. Dynamic variable selection in SNP genotype autocallign from APEX microarray data. BMC Bioinformatics vol. 7(521) 1471-2105.

* cited by examiner

*Primary Examiner*—Young J Kim
(74) *Attorney, Agent, or Firm*—Dodds & Associates; John Dodds; L. Susanne Somersalo (57) ABSTRACT

A genotyping method and a prepared oligomicroarray as device is to determine single nucleotide polymorphism (SNP) and mutations are provided. The method uses two specific APEX-2 primers per each SNP or mutations to be determined. The same primers are used in amplification phase (primer extension and PCR with universal primer) and in the single base extension phase on an array. All SNP-containing sequences can be genotyped and amplified in one reaction tube and visualized on a microarray.

21 Claims, 10 Drawing Sheets

Infinium I
Allele-Specific Primer Extension

Infinium II
Single Base Extension

A Insertions

B Deletions

```
                          SEQUENCE LISTING

<160> NUMBER OF SEQ ID NOS: 3

<210> SEQ ID NO 1
<211> LENGTH: 21
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(21)
<223> OTHER INFORMATION: universal primer sequence

<400> SEQUENCE: 1
gatcaggcgt ctgtcgtgct c                                              21

<210> SEQ ID NO 2
<211> LENGTH: 26
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(26)
<223> OTHER INFORMATION: primer

<400> SEQUENCE: 2
gattgagctg ctgcttttct ctcctt                                         26

<210> SEQ ID NO 3
<211> LENGTH: 23
<212> TYPE: DNA
```

-continued

```
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(23)
<223> OTHER INFORMATION: primer

<400> SEQUENCE: 3
ccctgcctca cacctgatag cac                                              23
```

METHOD TO DETERMINE SINGLE NUCLEOTIDE POLYMORPHISMS AND MUTATIONS IN NUCLEIC ACID SEQUENCE

PRIORITY

This application is a Continuation in Part application of the International Patent Application number PCT/EE2007/000003 which designates United States. The International patent application is incorporated herein by reference.

SEQUENCE DATA

This application contains sequence data provided on a computer readable diskette and as a paper version. The paper version of the sequence data is identical to the data provided on the diskette.

TECHNICAL FIELD OF THE INVENTION

This invention relates generally to genotyping technologies and mutation detection. More specifically this invention relates to methods to determine single nucleotide polymorphisms and mutations in genome. This invention is suitable for nucleic acid primary structure analyzes, for epigenetic effects and in molecular diagnostics.

BACKGROUND

Genotyping technologies enable to construct high-resolution genetic maps for genomes of human and other organisms, resulting in LD blocks or $r^2$ bins dependent of the method used. These LD blocks (haplotypes) can be used in association studies to localize genes responsible for a particular phenotype (e.g. disease). In other words, the aim of genotyping is to find correlations between genome organization (haplotype) and a particular phenotype.

It is becoming increasingly evident, that hundred thousands single nucleotide polymorphisms (SNP-s) have to be analyzed simultaneously to get a complete picture of haploblocks' (or $r^2$ bin) arrangement. Thus, new methods are needed to accomplish this expansive and expensive task. Below is an overview of well-known genotyping methods that despite of their high throughput technology have also their limiting factors and therefore new cost-effective, flexible and focused genotyping methods are needed.

Genotyping and mutation detection is increasingly more substantial in clinical practice. Modern and reliable methods are alternative for RFLP, allele-specific PCR or sequencing in future. Flexible genotyping and mutation detection analyzes systems help to diagnose tens of candidate genetic markers in one reaction in short time as a routine procedure.

1. Detection based hybridization methods such as Affymetrix GeneChip (FIG. 1.) technology enables to analyze half a million SNP-s (Matsuzaki et al., 2004 1 & 2). Studied loci in genomic DNA are amplified without PCR with specific primers. An alternative way to reduce complexity of the genome is to use the restriction enzyme cut of genomic DNA, ligation of the fragments produced in this way to a universal linker and amplification with universal primers in PCR. Amplified regions are fragmented, labeled and hybridized to complementary oligonucleotides synthesized on microarray. In case of a perfect match, a duplex is formed and a signal from the perfect match pairings which is higher than signals from the mismatched pairing is detected. GeneChip microarray uses 25 base pairs (bp) long oligonucleotides containing a central nucleotide corresponding to the studied SNP. Hence, on both sides of a SNP, there are regions with 12 bp perfect match and in the middle, at the position of the SNP, a perfect match or a mismatch can occur.

Figure 1:
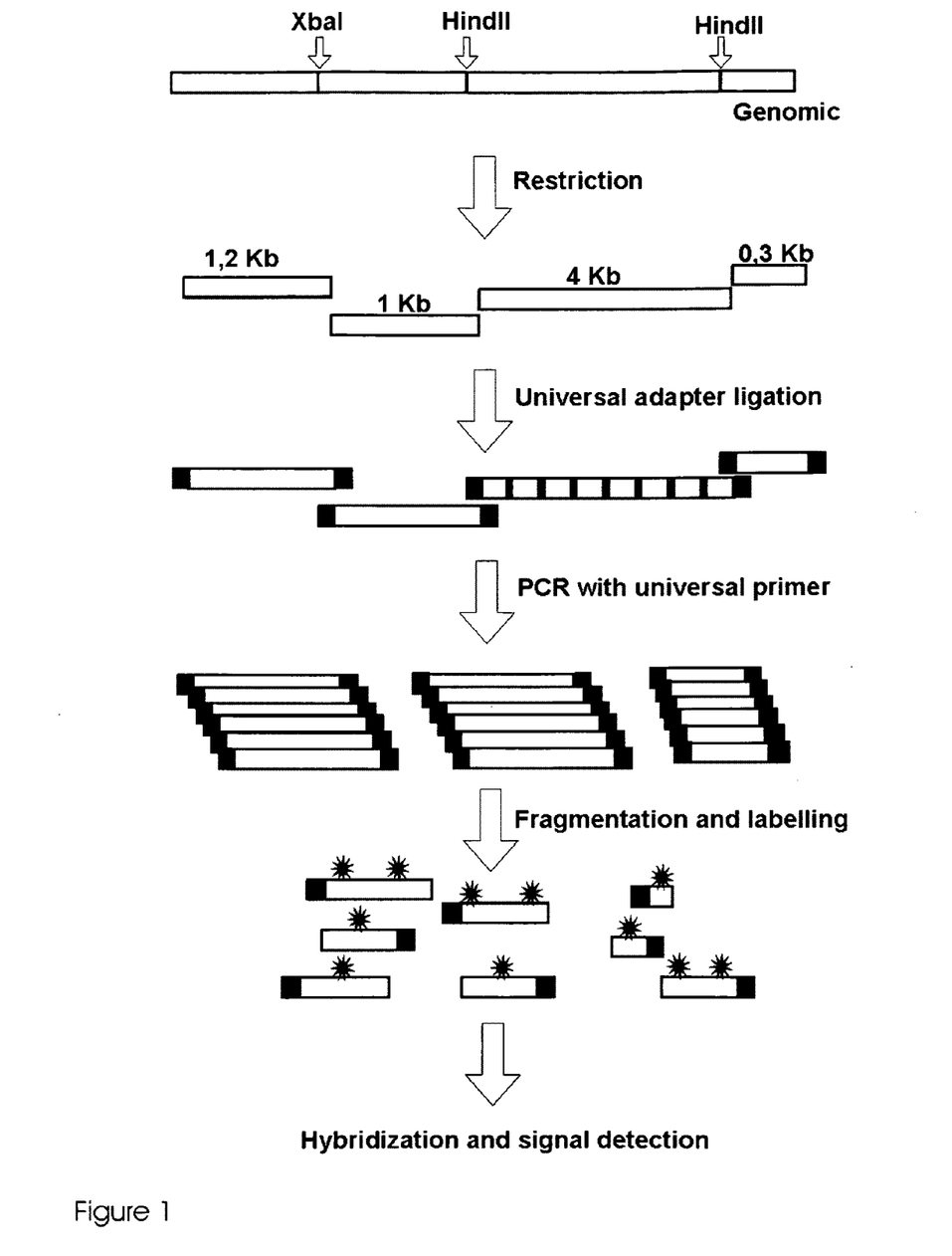
FIG. 1 schematically shows the known method of Affymetrix GeneChip.

The key step of the method is DNA restriction and addition of universal linker sequences to the ends of all created fragments. Subsequently 250-2000 bp long fragments, containing the SNP(s) of interest are amplified with primers that anneal to the universal linker sequences (universal primer). With this approach a vast number of genomic sequences can be amplified with minimal cost. The limiting factor in this method is the number of restriction sites across the genome. Thus, SNP-s not located in the synthesized fragments (250-2000 bp), cannot be detected. Hence, this method in principle does not cover the whole genome and therefore the Illumina 300K array is as informative as Affymetrix 500K array in CEU population (Barrett and Cardon, 2006).

Figure 2:
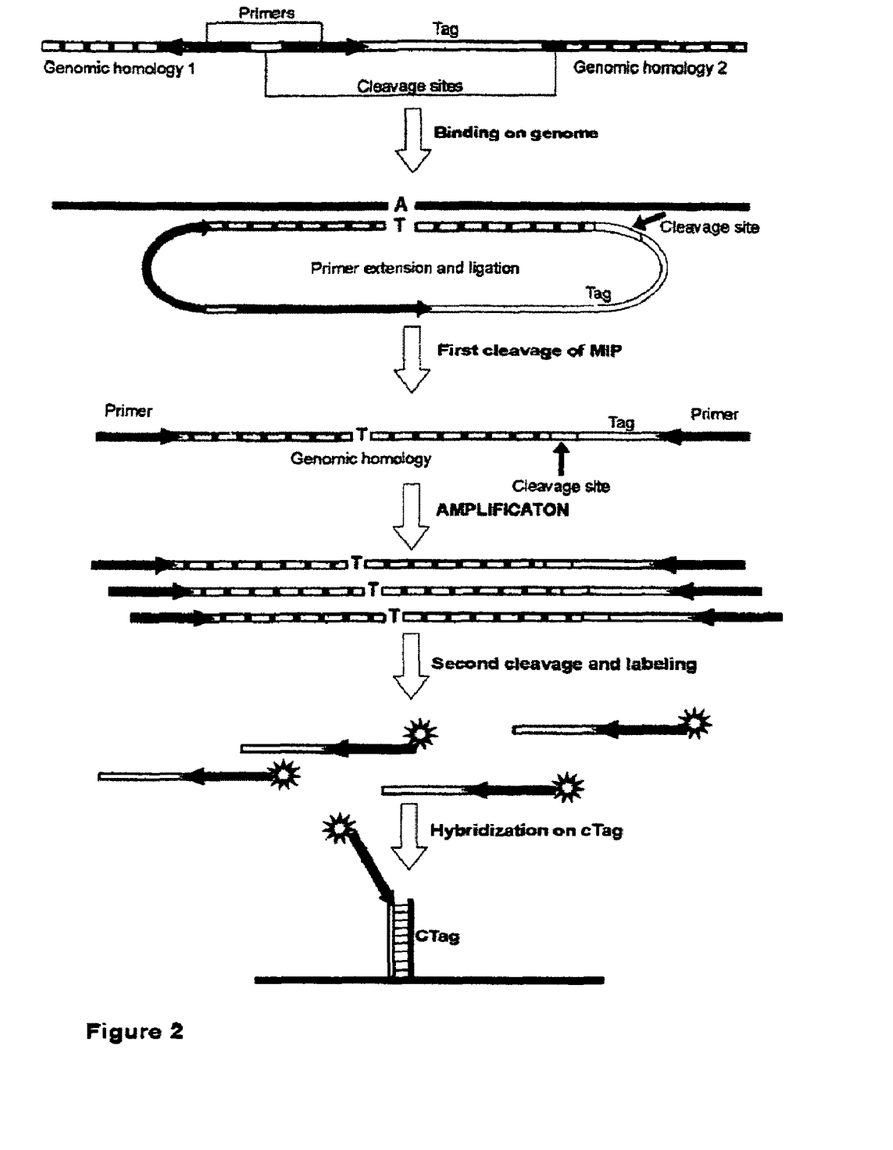
FIG. 2 schematically shows the principle of Affymetrix MIP method.

2. Affymetrix Molecular Inversion Probe (MIP) method uses MIP molecules which are special "padlock" probes (Nilsson et al., 1994) for genotyping. MIP molecule is a linear oligonucleotide that contains specific regions, universal sequences, restriction sites and a Tag (index) sequence (16-22 bp). MIP hybridizes directly around the genetic marker/SNP of interest (FIG. 2).

MIP method uses 1500 "padlock" probe sets that hybridize to genomic DNA in parallel (Hardenbol et al., 2003). In case of a perfect match, binding genomic homology regions are ligated by creating a circular molecule. After the first restriction, all molecules are amplified with universal primers. Amplicons are restricted again to ensure short fragments for hybridization on microarray. Generated short fragments are labeled and through Tag sequence hybridized to cTag (complementary strand for index) on array. After the formation of Tag-cTag duplex, a signal is detected.

Despite the complexity of experimental procedures, it is possible to amplify up to 10 000 SNP-containing sequences in one reaction. Thereby polymorphisms can theoretically be detected in any genomic region of interest (Hardenbol et al., 2005). There are two MIP probes for each allele, thus the method uses four probes (70 to 100 bp), a universal primer and a cTag sequence on array for a SNP detection in both strand.

Figure 3:
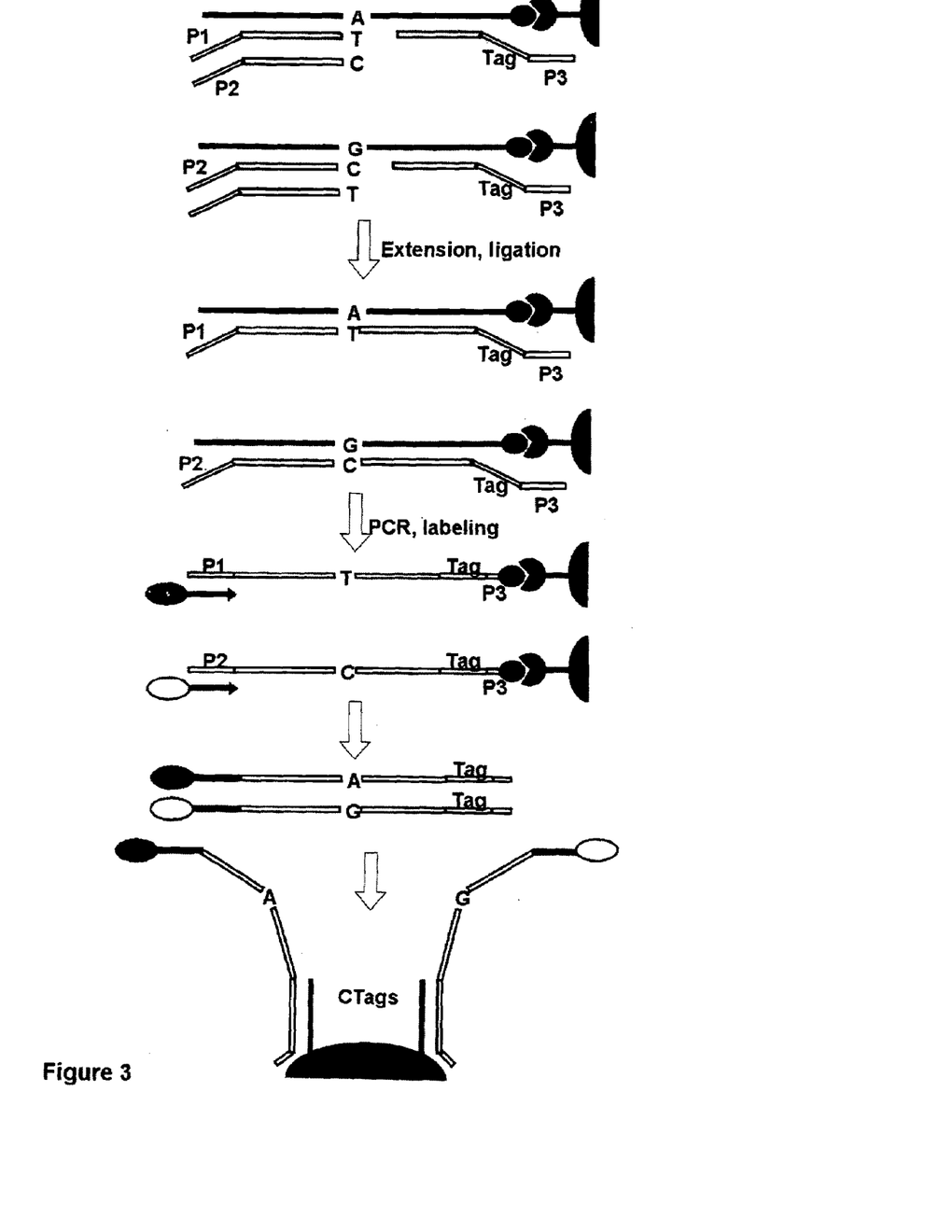
FIG. 3 schematically shows that principle of Illumina Bead Chip method.

3. Illumina GoldenGate genotyping platform outstands primarily with an original solution of the gene chip, but the molecular approach amplifying genomic regions is similar to MIP probes. Genomic DNA fragments are attached to specific particles, followed by hybridization with specific probe molecules (FIG. 3). Probe molecules are supplied with three different universal sequences and a Tag sequence, situated between the specific region and universal primer (Gunderson et al., 2005). Specific primers are hybridized to genomic DNA and designed to be allele specific, meaning that in order to identify a SNP, an oligonucleotide must be synthesized in a way that its 3' end binds to the SNP under study.

Hence, to determine a SNP two probe molecules, each supplied with a different universal primer sequence, are needed. In case of a 3' perfect base-pairing at the 3'-end one primer is elongated by primer extension reaction up to the other oligonucleotide, followed thereafter by ligation and generation of a linear molecule. The formed molecule includes two universal primer binding sites and a Tag sequence.

The formation of a linear molecule enables the PCR amplification with universal primers which in turn are supplied with two different fluorescence labels to detect homo- or heterozygosity at the studied position. GoldenGate method uses hybridization-based signal detection through formation of Tag-cTag complex.

4. The Infinium 1 method of Illumina (FIG. 4) enables similarly to Affymetrix GeneChip technology a genome-wide analysis and to test up to half a million SNPs on a gene chip so far. The method does not use PCR to amplify the studied loci. Instead, genomic DNA is amplified using the WGA method (*Whole Genome Amplification*) (Gunderson, Steemers et al., 2005).

Figure 4:
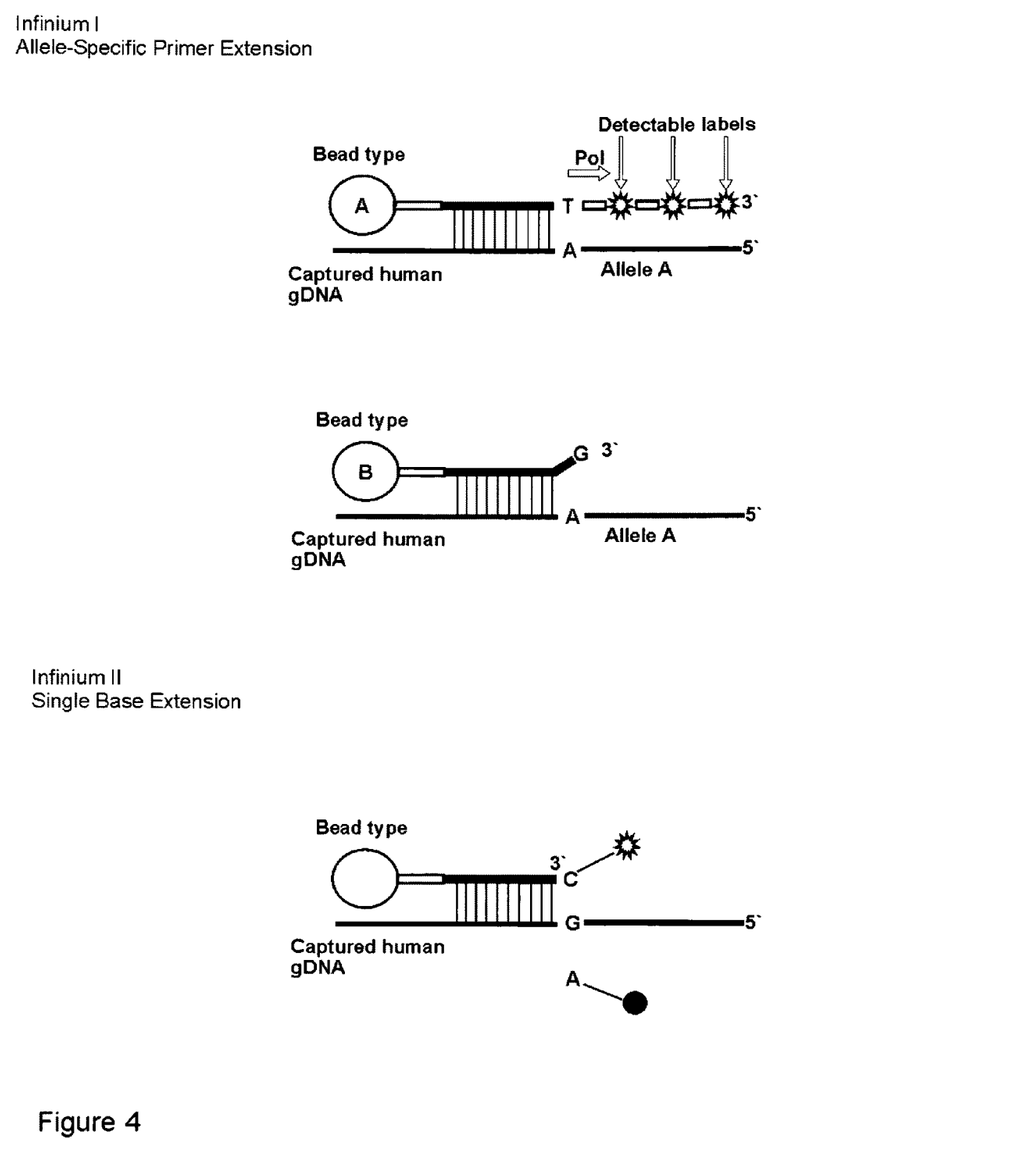
FIG. 4 schematically shows the principle of Illumina Infinium 1 and 2 method.

Amplified genomic DNA is fragmented and hybridized to oligonucleotides (75 bp) on the gene chip. After hybridization from 16 to 18 hours, unbound or mismatched fragments are removed during a specific wash step.

The studied genotype on the gene chip is determined by using allele-specific oligonucleotides (Infinium1), where the 3'-terminal nucleotide is complementary to the SNP and which are primer extended away from the marker. In case of a perfect match primer sequence is elongated by DNA polymerase with fluorescence-labeled desoxynucleotides, which in case of the switch in the chain give a fluorescence signal. In order to detect a SNP two oligonucleotides are used on a gene chip.

Infinium 2 platform incorporates two-color single base extension to detect a single nucleotide polymorphism with 100K BeadChip, using only one oligonucleotide per SNP (Steemers et al., 2006).

Compared to GeneChip technology Infinium 1 and 2 are not defined by the restriction sites in genomic DNA and therefore has a good potential to solve the genotyping of all SNPs.

DESCRIPTION OF PREFERRED EMBODIMENTS

The method according to this description is a genotyping and mutation analysis method that enables a robust, flexible, cost-effective SNP and mutation analysis accompanied with high fidelity. The method is hereinafter called APEX-2 (Arrayed Primer Extension using Universal primer). APEX-2 is very well suited for a focused study with 15 to 1500 SNPs or mutations. In principle, all SNP-containing sequences can be amplified in one reaction tube and further genotyped on a microarray by single base extension.

Figure 5:
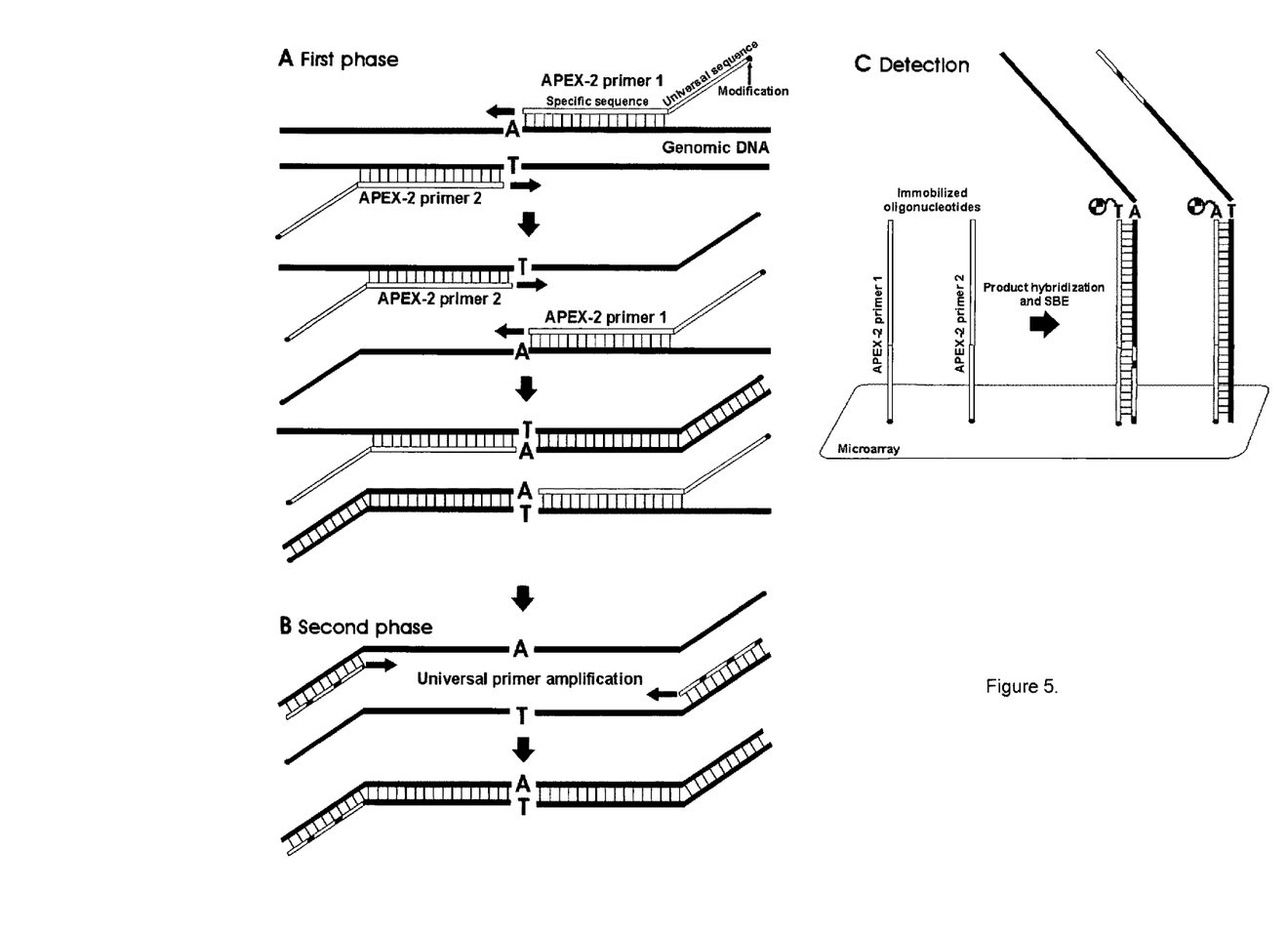
FIG. 5 schematically shows the principle of APEX-2 and three main phases (preferred embodiment).

APEX-2 method, according to preferred embodiment, enables template amplification through high levels of multiplexing PCR in two phases: primer extension (First phase) and PCR with universal primers (Second phase) (FIG. 5). That means, in the first step a specific primer extension product will be obtained where SNP under question has been analyzed, in the second step we just increase the amount of this product using universal primer in order to have enough molecules to be detected in signal detector. Only new information in this amplicon is the SNP (or mutation site) itself. In detail, in the first phase, the method uses two specific primers for determination of one SNP. These primers are called APEX-2 primers. One of the APEX-2 primers binds to the coding DNA strand and the other to its complementary DNA strand. After primer extension in the first phase the APEX-2 pre-product is formed. The Pre-product contains two APEX-2 primer sequences, complementary sequences for APEX-2 primers and studied nucleotide pair in the middle of the two primers (see FIG. 5). In this case only one new non primer (genomic SNP or mutation) nucleotide will be amplified. The second phase (universal primer PCR) is essential for amplification of the pre-products. The universal primer PCR amplification step is only for completely synthesized pre-products. Universal primer is identical to the universal part of APEX-2 primer and thus can bind to synthesized complementary sequence of APEX-2 primer.

Figure 6:
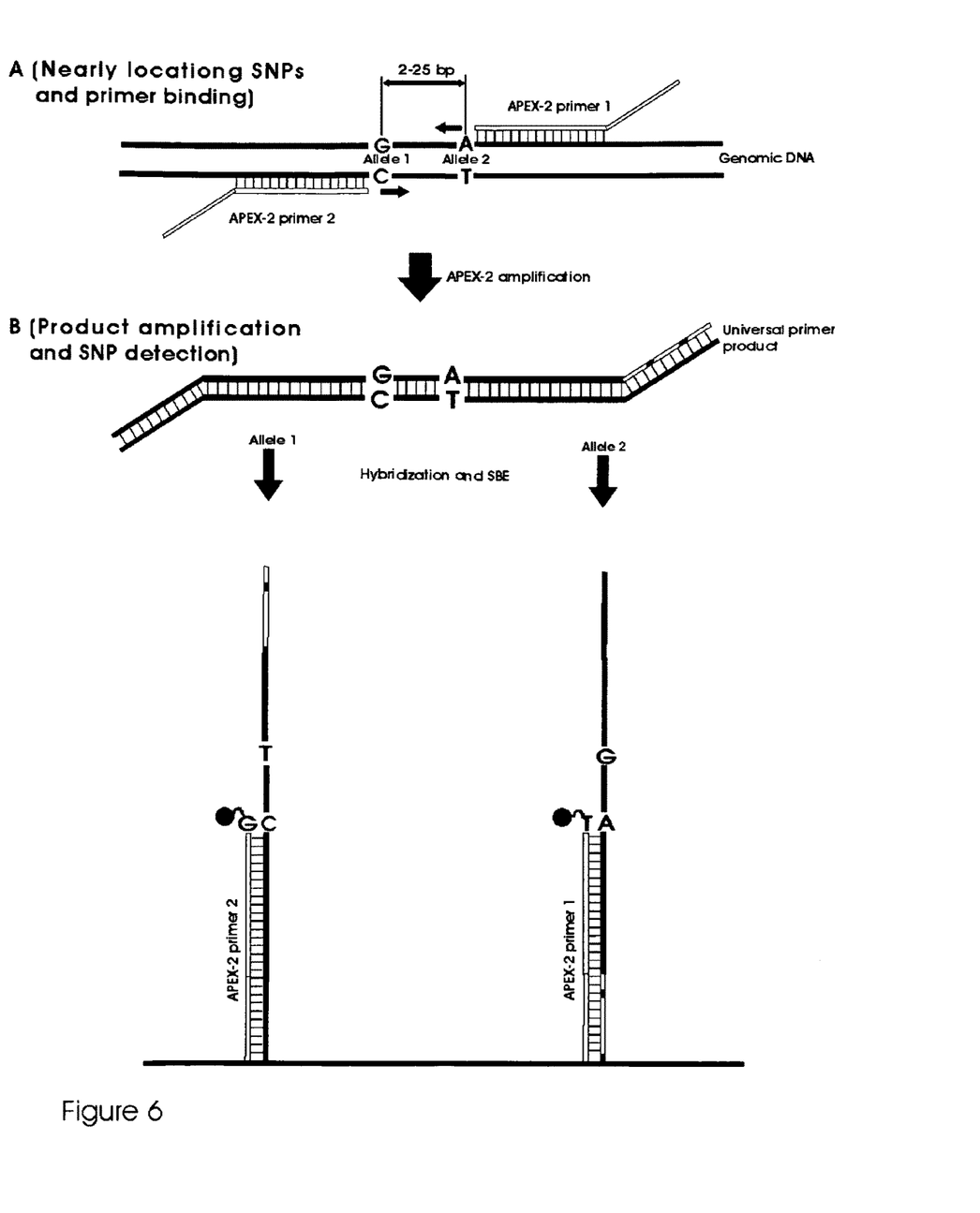
FIG. 6 schematically shows the principle of APEX-U, second embodiment.

According to another preferred embodiment (FIG. 6) the method uses two specific primers (APEX-2 primers) for detection of two SNPs in close proximity to each other. In this case more than one non-primer nucleotide (2-25) is amplified in the first phase depending on the distance between the SNPs. The principles of second- and third phase are same for the embodiment described above and this embodiment.

Figure 7:
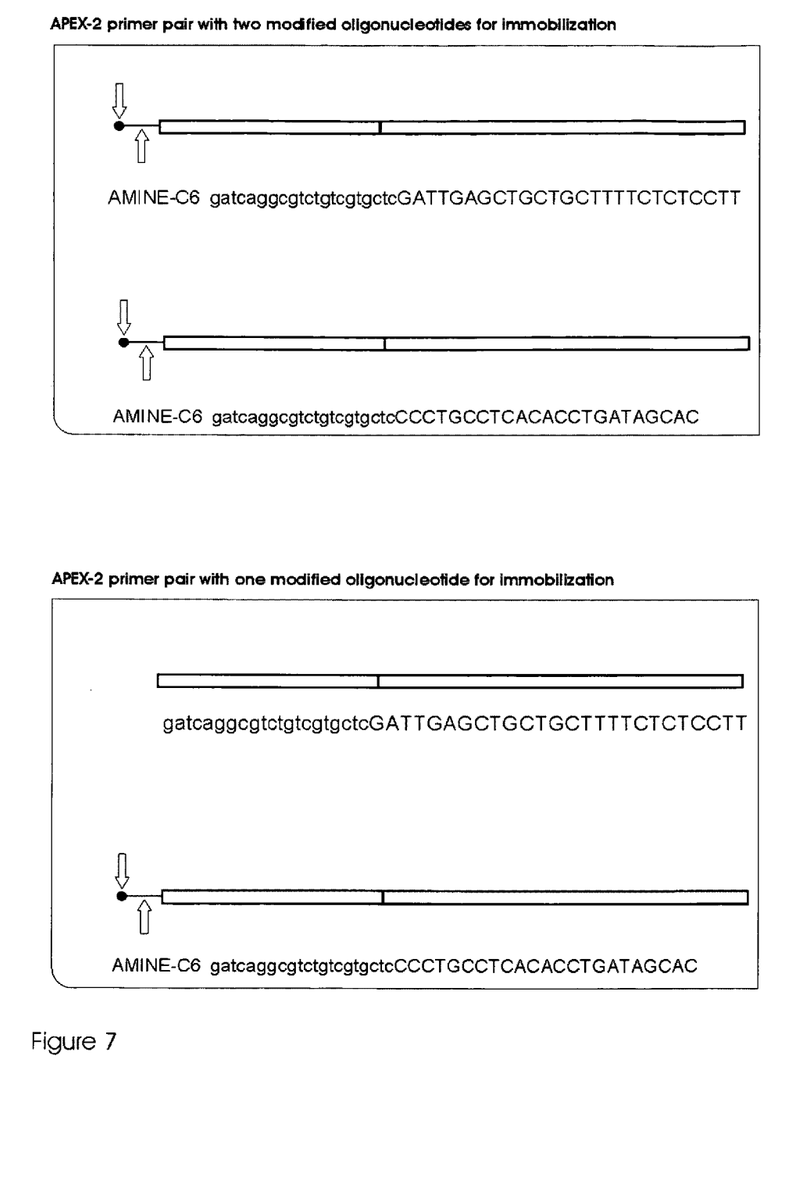
FIG. 7 schematically shows an example of the APEX-2 primer structure. In this example the universal sequence has sequence gatcaggcgtctgtcgtgctc (SEQ ID NO:1); the first APEX-2 primer has sequence gattgagctgctgcttttctctcctt (SEQ ID NO:2) and the second APEX-2 primer has sequence ccctgcctcacacctgatagcac SEQ ID NO:3)

Each APEX-U-primer consists of two specific sequence regions: 3' complementary sequence for template nucleic acid (genomic DNA, cDNA, RNA), and a universal sequence for large-scale amplification and an optional modification in the 5' end (attached via linker) (FIG. 7) to enable primer immobilization on microarray. Therefore, determination of one SNP or determination of two SNPs locating close to each other requires two specific oligonucleotide sequences and one universal sequence in amplification and in detection on microarray.

Figure 8:
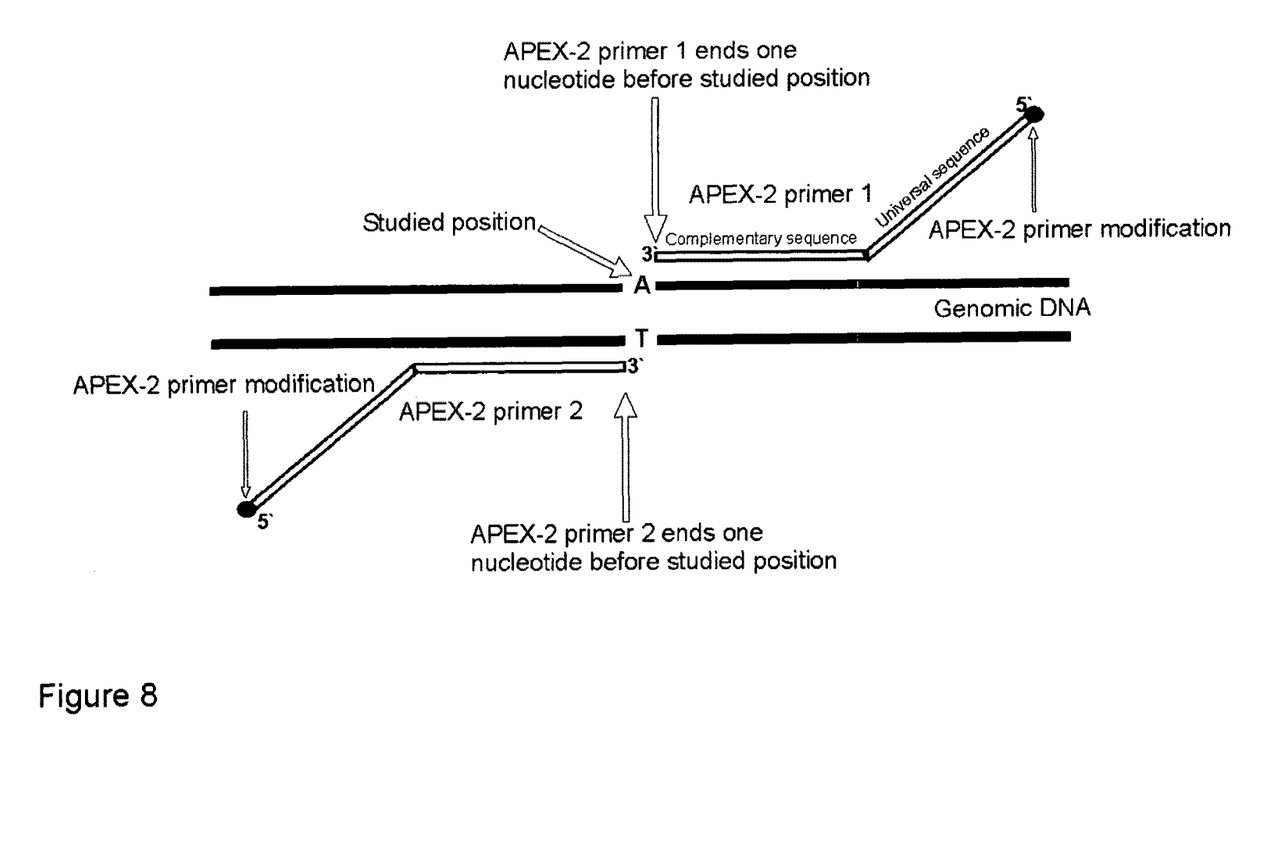
FIG. 8 schematically shows binding of the specifically designed primers to genomic DNA and their location with respect to the studied SNP or mutation in the APEX-2 system.

The primers according to this invention are designed in the way that the 3' end of the primer terminates at the nucleotide before the studied SNP or mutation. As according to one preferred embodiment (FIG. 8), only one nucleotide from target nucleic acid is being amplified after the first and the second phase on APEX-2 reaction. According to another preferred embodiment (FIG. 6), the primers are designed so that APEX-2 primer 1 for coding DNA strand terminates at the nucleotide before the studied allele 2 position and APEX-2 primer 2 for complementary DNA strand terminates at the nucleotide before the studied allele 1 position.

In the third phase (detection), the SNPs or mutations are detected through single base extension on an array where the primers have same design as the primers of the binding phase. In other words, detection on microarray uses the same oligonucleotides (attached to solid phase) as used in APEX-2 amplification (in liquid phase).

Primer extension in the first APEX-2 phase and single-base extension in detection phase enable to detect di, -tri or quatro allelic mutations or SNPs. APEX-2 primer ends one nucleotide before the studied position and all four nucleotides (A, T, C, G) which are complementary to template nucleic acid are possible in primer extension. In the detection step, APEX-2 uses four labeled nucleotides (A, U, C, G) as in published APEX method (Kurg et al., 2000).

Figure 9:
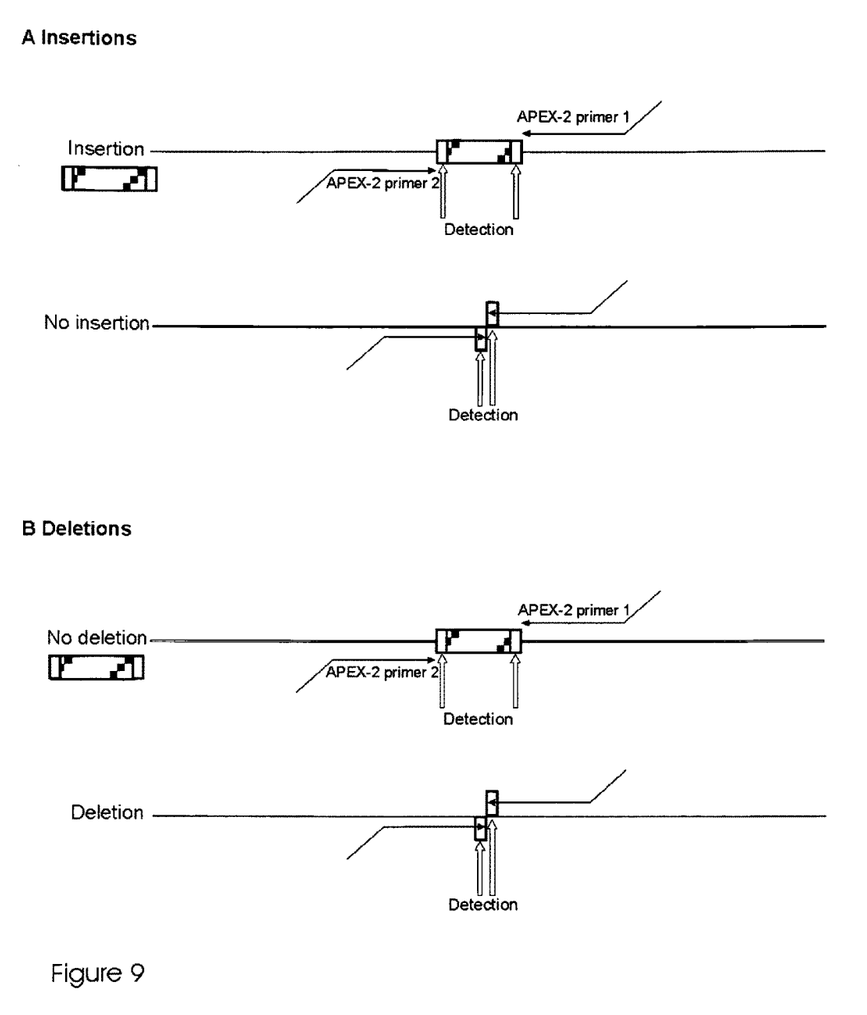
FIG. 9 schematically shows detection of mutations (insertion and deletion) in the APEX-2 system.

APEX-2 method is suitable for SNP- as well as for single nucleotide mutation (i.e. one nucleotide substitutions, insertions, deletions) analysis. APEX-2 method also enables detection of 2-25 nucleotide long deletions or insertions by using APEX-2 primers which are designed in a way that the primer 3' end terminates one nucleotide before the studied region and the first nucleotide of the insertion sequence or one nucleotide substitution is detected (FIG. 9A). In case of a deleted region or single nucleotide deletion, APEX-2 primer 3' end terminates one nucleotide before the studied deletion and the first nucleotide of the opposite APEX-2 primer is detected (deletion) (FIG. 9B). As comparison, a wild type sequence is used, where no deletion has taken place. In this case, the first nucleotides of both ends of the deletion region are detected (FIG. 9A).

APEX-2 method differs from Affymetrix MIP probe and Illumina GoldenGate techniques as follows:

a) ligation reaction is not needed b) highly multiplex PCR (in principle 15 to 1500-plex) is used.

c) APEX-2 primers are used for PCR and for single base extension on the microarray d) index sequences (tag and ctag) are not needed Another difference between the method according to this invention and any prior art disclosures is the primer-target architecture—the primer ends one nucleotide before the studied SNP or mutation in first and second phase amplification and also in detection phase on microarray (single base extension). Thus, no allele-specific primers are needed for SNP detection and only two primer sequences are essential for amplification and detection of both the alleles of the nucleic acid.

APEX-2 primers used in the first phase of APEX-2 and detection step have a modification at their 5' end (attached via linker), which enables to spot the same primers (or primer) on a microarray and to detect the appropriate SNP or mutation by single base extension with fluorescently labeled ddNTP-s.

EXAMPLE 1

Figure 10:
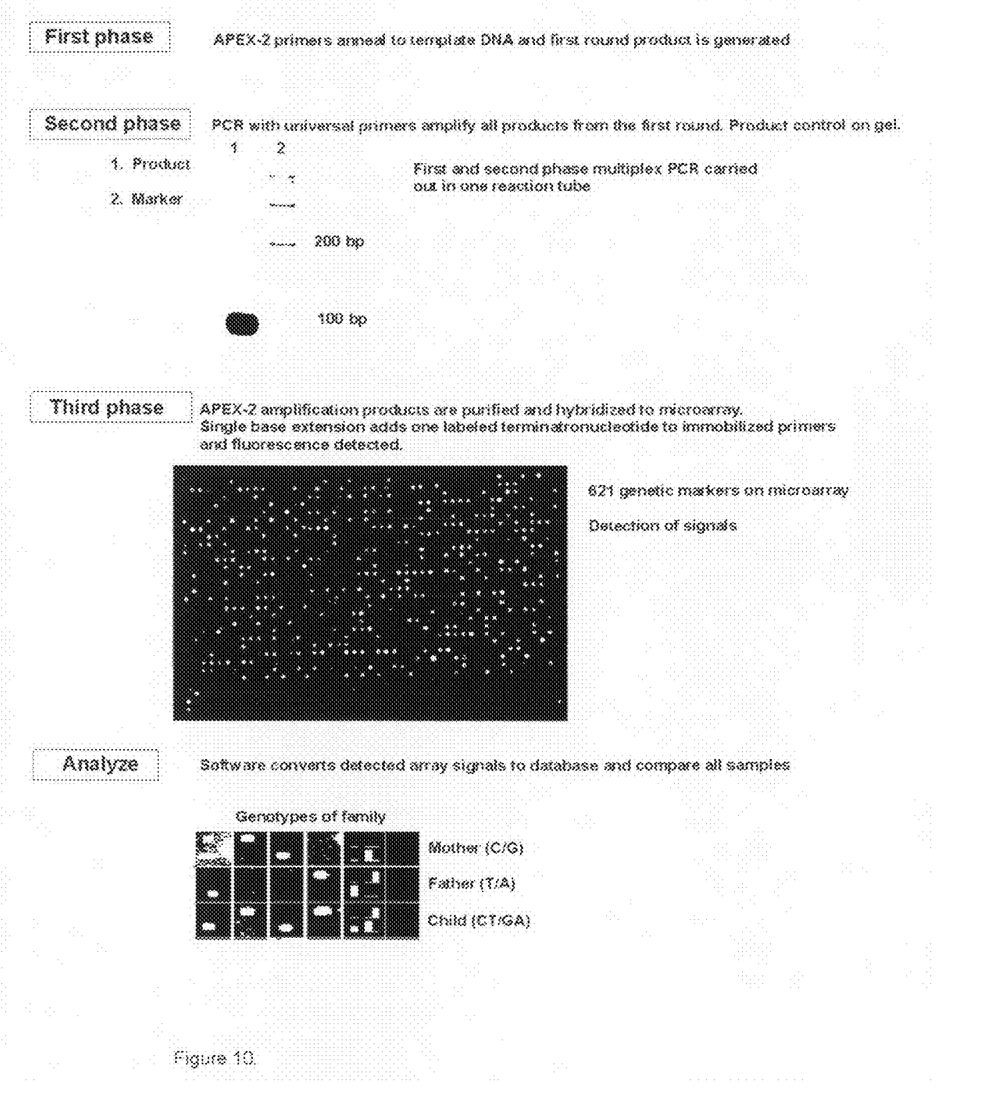
FIG. 10 illustrates visualization of the proof of principle for APEX-2 genotyping method using 621 genetic loci

The first example describes amplification of the SNPs or mutations under study (FIG. 10).

To amplify all SNPs in highly multiplex PCR reaction, genomic DNA was diluted in TE buffer (10 mM Tris (pH 8.0), 1 mM EDTA) to 100 ng/µl, denaturized for 5 minutes at 98° C. and cooled down to room temperature just before PCR. Multiplex PCR was carried out in 20 µl volume that contained PCR buffer (60 mM Tris-HCl (pH 8.3), 60 mM KCl, 15 mM $(NH_4)_2SO_4$) (Fermentas), 0.2 mM each desoxynucleotide (G, C, A, T), 5 mM $MgCl_2$, 2 U TrueStart DNA polymerase (Fermentas), 30 nM each specific primer (Metabion) and 200 ng genomic DNA. Twenty-four cycles of PCR were run on GeneAmp PCR System 9700 (Applied Biosystems) thermocycler: initial denaturation and TrueStart DNA polymerase activation 5 minutes at 98° C., denaturation at 95° C. for 30 sec, annealing at 56° C. for 20 sec, extension at 72° C. for 20 sec and final extension for 5 minutes at 72° C. Time between annealing and extension step is 6.5 minutes (ensured by 3% ramp speed). First, PCR products created using specific primers are the templates for universal primer amplification in phase two. Universal primer amplification is carried on in 150 µl volume that includes 20 µl of first phase PCR product. Mixture (130 µl) contains PCR buffer (80 mM Tris (pH 9.5) 20 mM $(NH_4)_2SO_4$, 0.2% w/v Tween-20) (Solis Biodyne), 3.5 mM each nucleotide, 3.5 mM $MgCl_2$, 15 HotFire DNA polymerase (Solis Biodyne) and 40 µM universal primer (GATCAGGCGTCTGTCGTGCTC) (SEQ ID NO:1). Initial enzyme activation and denaturation last for 15 minutes at 95° C., denaturation at 95° C. for 30 sec, annealing at 54° C. for 30 sec, extension at 72° C. for 5 sec and after twenty cycles final extension for five minutes at 72° C. As a check, 1 µl of PCR product is visualized on 2.5% TBE agarose gel to confirm the size range of amplicons (FIG. 9). PCR products from universal primer amplification are purified using the MinElute Purification kit (Qiagen) under modified protocol. 600 µl binding buffer is mixed with 150 µl of PCR product. 5 µl 5.4 M (pH 5.0) of sodium-acetate is added to guarantee the optimum pH for the spin column. Products are eluted with 23 µl EB buffer (Qiagen).

EXAMPLE 2

This second example describes the single base extension on microarray (FIG. 10, detection and analyze)

Alkaline phosphatase (SAP) treatment is essential before primer extension with didesoxynucleotides to eliminate active desoxynucleotides in this reaction. 3 µl of 10× ThermoSequenase™ (Amersham Bioscience) reaction buffer and 0.5 U SAP (Fermentas) is added to purify the PCR product. Mixture is incubated for 15 minutes at 37° C. and SAP is inactivated during heating for 10 minutes at 95° C. This incubation is also as template denaturation phase before primer extension on array. After 10 minutes of denaturation at 95° C. 1.25 µM didesoxynucleotide mixture (Cy3-ddATP; Cy5-ddGTP; Texas Red®-ddCTP and Fluoresceine-12-ddUTP (Perkin Elmer Life Science)), 5 U of ThermoSequenase™ DNA polymerase (Amersham Biosciences) and 3 mM $MgCl_2$ in the final volume of 30 µl are added. Mixture is applied to the pre-warmed arrays on a heat-plate and the arrays are covered with LifterSlip™ ((22×25 mm) Erie Science Company). The hybridization and APEX reaction is performed at 58° C. for 20 minutes and terminated by washing at 95° C. for 1 min in Milli-Q water, followed by washing for 3 min in 0.3% Alconox® solution (Alconox). Alconox is removed by washing the arrays two times for 1 min with 95° C. Milli-Q water. To reduce bleaching, 12 µl SlowFade® antifade reagent (Invitrogen) is applied to the slide. The arrays are scanned with the Genorama® imaging system (Asper Biotech) at 20 µm resolution.

EXAMPLE 3

Specificity and Other Parameters of APEX-2

To measure the specificity (Type I error) of APEX-2, genotypes were compared with another approved genotyping method (Illumina). The coincidence between Illumina HumanCNV370-Duo v1.0 BeadChips and APEX-2 genotyping was measured with 173 SNPs genotyped with both methods in 19 individuals. The call-rates of the Illumina and APEX-2 were 99.33% and 99.24% accordingly. The number of SNPs which were successfully genotyped with both methods was 3240, the coincidence rate between two platforms was 98.6% and Type I error rate was 1.4%.

Call-rate is a parameter of genetic allele detection systems, which is determined by the percent of how many observed genetic positions were detectable. In APEX-2 we genotyped successfully 139 424 positions of 139 606 and the call-rate was 99.87%. To assess reproducibility, nine randomly chosen individuals were each independently genotyped five times. Missing calls were distributed equally over the examined DNAs and the rate was 99.92%.

Minimal genomic DNA amount (in nanograms) is substantial parameter which is required to determine the genotypes without previous whole genome amplification procedure. The APEX-2 required 1-10 nanograms of genomic DNA to provide 99.2% call-rate through experiments. Between the range of 0.1-1 nanograms, the call-rate decreased to 84.6%. The minimal genomic DNA amount is for example relevant in forensic analysis and in molecular diagnostics of infants. In other cases, generally a higher amount (100-300 nanograms) of genomic DNA is used.

REFERENCES

Barrett J C, Cardon L R. Evaluating coverage of genome-wide association studies. Nat Genet. 2006 June; 38(6):659-62

Fan, J. B. et al Highly parallel SNP genotyping. Cold Spring Harb. Symp. on Quant. Biol. LXVII, 69-78 (2003).

Gunderson, K. L., Steemers, F. J., Lee, G., Mendoza, L. G. & Chee, M. S. A genome-wide scalable SNP genotyping assay using microarray technology. Nat. Genet. 37, 549-554 (2005).

Hardenbol, P. et al. Highly multiplexed molecular inversion probe genotyping: Over 10,000 targeted SNPs genotyped in a single tube assay. Genome Res. 15, 269-275 (2005).

Hardenbol, P. et al. Multiplexed genotyping with sequence-tagged molecular inversion probes. Nat. Biotechnol. 21, 673-678 (2003).

Kurg, A., N. Tonisson, et al. (2000). Arrayed primer extension: solid-phase four-color DNA resequencing and mutation detection technology. Genet Test 4(1): 1-7.

Matsuzaki, H. et al. Genotyping over 100,000 SNPs on a pair of oligonucleotide arrays. Nat. Methods 1, 109-111 (2004).

Matsuzaki, H. et al. Parallel genotyping of over 10,000 SNPs using a one-primer assay on a high-density oligonucleotide array. Genome Res. 14, 414-425 (2004).

Nilsson, M. et al. Padlock probes: circularizing oligonucleotides for localized DNA detection. Science 265, 2085-2088 (1994).

Steemers F J et al., Whole-genome genotyping with the single-base extension assay, Nat Methods. 2006 January; 3(1):31-3.

What is claimed is:

1. A method to determine single nucleotide polymorphism (SNP) in a target nucleic acid sequence, said method comprising the steps of:
   a) providing a template nucleic acid, consisting of a first and a second strand and having one unknown nucleotide pair;
   b) APEX-2 (Arrayed Primer Extension using Universal primer) oligonucleotide primer;
      said first APEX-2 primer consisting of a first specific oligonucleotide sequence in its 3'-end and a universal sequence in its 5'end, said universal sequence further having a modification in its 5'end, and said first specific oligonucleotide sequence being complementary to nucleotides before the unknown nucleotide in the first strand of the template nucleic acid;
      said second APEX-2 primer consisting of a second specific oligonucleotide sequence in its 3'-end and a universal sequence in its 5'end, said universal sequence optionally having a modification in its 5'end and, said second specific oligonucleotide sequence being complementary to nucleotides before the unknown nucleotide in the second strand of the template nucleic acid;
   c) amplifying the unknown nucleotide of the first and the second strand of the template nucleic acid by running a multiplex PCR primer extension reaction with the first and the second APEX-2 primers as templates, thereby producing a first amplification product, said first amplification product consisting of a first and a second strand, said first strand consisting of sequence of the first APEX-2 primer and a complementary sequence to the second APEX-2 primer and the unknown nucleotide between them, and the second strand consisting of complementary sequence to the APEX-2 first primer and the sequence of the second APEX-2 primer and the unknown nucleotide between them;
   d) amplifying the first amplification product in a PCR reaction with universal primer as template, thereby producing a second amplification product;
   e) providing a microarray of probes, where probes are identical to the first and the second APEX-2 primers of step b) and where the probes are immobilized on the array by attaching them to a solid surface from the modified 5'end;
   f) letting the second amplification products anneal with immobilized probes and providing labeled or modified terminator nucleotides for single base extension reaction; and
   g) identifying terminating nucleotide that has been added to the probes, said terminating nucleotides corresponding to the unknown nucleotides of the template nucleic acid.

2. The method according to claim 1, wherein the template nucleic acid has a first and a second pair of unknown nucleotides in proximity of 2 to 25 bp to each other and wherein the first specific oligonucleotide sequence is complementary to nucleotides before unknown nucleotide of the first nucleotide pair on the first nucleic acid strand and the second specific oligonucleotide sequence is complementary to nucleotides before unknown nucleotide of the second nucleotide pair of the second nucleic acid strand.

3. The method according to claim 1, wherein the universal sequence of both the first and the second APEX-2 primers have a modification in its 5' end.

4. The method of claim 1, wherein only two cycles of amplification are used to produce the first amplification product in step c).

5. The method of claim 1, wherein the modification in the 5'end of the first specific primer and/or the second specific primer are attached with a linker.

6. The method of claim 5, wherein the linker is Amine-C6.

7. The method of claim 1, wherein the template nucleic acid is selected from a group consisting of genomic DNA, cDNA and RNA.

8. The method of claim 1, wherein the solid surface is made of a material selected from the group consisting of glass, plastic, beads, and paper.

9. The method of claim 1, wherein the unknown nucleotide pair is di, -tri or quatro allelic mutation or SNP.

10. The method of claim 1, wherein the unknown nucleotide pair is an insertion and the identifying terminating nucleotide of step g) corresponds to first nucleotide of insertion sequence.

11. The method of claim 1, wherein the unknown nucleotide pair is a deletion and the identifying terminating nucleotide of step g) corresponds to first nucleotide of opposite APEX-2 primer.

12. The method according to claim 1, wherein the universal sequence is according to SEQ ID NO:1.

13. The method according to claim 2, wherein the universal sequence of both the first and the second APEX-2 primers have a modification in its 5' end.

14. The method of claim 2, wherein only two cycles of amplification are used to produce the first amplification product in step c).

15. The method of claim 2, wherein the modification in the 5'end of the first specific primer and/or the second specific primer are attached with a linker.

16. The method of claim 2, wherein the template nucleic acid is selected from a group consisting of genomic DNA, cDNA and RNA.

17. The method of claim 2, wherein the solid surface is made of a material selected from the group consisting of glass, plastic, beads, and paper.

18. The method of claim 2, wherein the unknown nucleotide pair is di, -tri or quatro allelic mutation or SNP.

19. The method of claim 2, wherein the unknown nucleotide pair is an insertion and the identifying terminating nucleotide of step g) corresponds to first nucleotide of insertion sequence.

20. The method of claim 2, wherein the unknown nucleotide pair is a deletion and the identifying terminating nucleotide of step g) corresponds to first nucleotide of opposite APEX-2 primer.

21. The method according to claim 2, wherein the universal sequence is according to SEQ ID NO: 1.

* * * * *